United States Patent
Uematsu et al.

(10) Patent No.: US 8,478,395 B2
(45) Date of Patent: Jul. 2, 2013

(54) METHOD OF MEASURING ELECTRICAL RESISTANCE VALUE OF CORNEAL TRANS-EPITHELIUM

(75) Inventors: Masafumi Uematsu, Nagasaki (JP); Takashi Kitaoka, Nagasaki (JP); Koji Nishida, Miyagi (JP); Yuji Tanaka, Miyagi (JP); Matsuhiko Nishizawa, Miyagi (JP); Hirokazu Kaji, Miyagi (JP); Soichiro Sekine, Miyagi (JP)

(73) Assignees: Nagasaki University, Nagasaki-shi (JP); Tohoku University, Sendai-shi (JP)

( * ) Notice: Subject to any disclaimer, the term of this patent is extended or adjusted under 35 U.S.C. 154(b) by 287 days.

(21) Appl. No.: 12/921,069

(22) PCT Filed: Mar. 3, 2009

(86) PCT No.: PCT/JP2009/053968
§ 371 (c)(1),
(2), (4) Date: Nov. 3, 2010

(87) PCT Pub. No.: WO2009/110470
PCT Pub. Date: Sep. 11, 2009

(65) Prior Publication Data
US 2011/0046509 A1    Feb. 24, 2011

(30) Foreign Application Priority Data
Mar. 3, 2008    (JP) .................. 2008-052567

(51) Int. Cl.
*A61B 5/053*    (2006.01)
(52) U.S. Cl.
USPC ........................................ 600/547

(58) Field of Classification Search
USPC ................................. 600/547, 558
See application file for complete search history.

(56) References Cited

U.S. PATENT DOCUMENTS

| | | | | |
|---|---|---|---|---|
| 4,381,007 A | * | 4/1983 | Doss | 606/27 |
| 4,691,715 A | * | 9/1987 | Tanne | 33/561.1 |
| 4,874,237 A | * | 10/1989 | Cringle | 221/221 |
| 4,951,683 A | * | 8/1990 | Davis | 600/383 |

(Continued)

FOREIGN PATENT DOCUMENTS

| | | |
|---|---|---|
| JP | 48-010716 Y | 3/1973 |
| JP | 03-503971 A | 9/1991 |
| JP | 2008154857 A * | 7/2008 |
| WO | WO 90/07902 A1 | 7/1990 |

OTHER PUBLICATIONS

"The effect of scleral recording location on ERG amplitude" Current Eye Research 5, 959-965 by Cringle, Alder, Yu.*
Chetoni et al., *Toxicology* in Vitro , 17: 497-504 (2003).

(Continued)

*Primary Examiner* — Sean P Dougherty
*Assistant Examiner* — Michael C Stout
(74) *Attorney, Agent, or Firm* — Leydig, Voit & Mayer, Ltd.

(57) ABSTRACT

The invention provides a method for evaluating a corneal disorder quantitatively and is applicable to living eyes. In particular, the invention provides a method for measuring a corneal transepithelial electric resistance, which method comprises: (1) a step of placing a first electrode on the cornea and a second electrode on the conjunctiva; and (2) a step of flowing an electric current between the first electrode and the second electrode to measure the electric resistance. The invention also provides a device for measuring a corneal transepithelial electric resistance value.

12 Claims, 6 Drawing Sheets

U.S. PATENT DOCUMENTS

| | | | | |
|---|---|---|---|---|
| 5,353,802 | A * | 10/1994 | Ollmar | 600/547 |
| 7,384,145 | B2 * | 6/2008 | Hetling et al. | 351/219 |
| 8,118,752 | B2 * | 2/2012 | Hetling et al. | 600/558 |
| 2002/0035388 | A1 * | 3/2002 | Lindemans et al. | 607/120 |
| 2004/0039297 | A1 * | 2/2004 | Abreu | 600/558 |
| 2005/0107780 | A1 * | 5/2005 | Goth et al. | 606/41 |
| 2006/0095108 | A1 * | 5/2006 | Chowdhury et al. | 607/141 |
| 2007/0005117 | A1 * | 1/2007 | Fritsch et al. | 607/56 |
| 2007/0106278 | A1 * | 5/2007 | Higuchi et al. | 604/891.1 |
| 2007/0142718 | A1 * | 6/2007 | Abreu | 600/323 |
| 2007/0142878 | A1 * | 6/2007 | Krulevitch et al. | 607/54 |
| 2007/0188710 | A1 * | 8/2007 | Hetling et al. | 351/221 |
| 2007/0260171 | A1 * | 11/2007 | Higuchi et al. | 604/20 |
| 2008/0294066 | A1 * | 11/2008 | Hetling et al. | 600/558 |
| 2009/0281451 | A2 * | 11/2009 | Hetling et al. | 600/558 |

OTHER PUBLICATIONS

Fukuda et al., *Journal of the Eye*, 24(4): 521-525 (2007).
Rojanasakul et al., *International Journal of Pharmaceutics*, 63: 1-16 (1990).
Rojanasakul et al., *International Journal of Pharmaceutics*, 66: 131-142 (1990).
Uematsu et al., *Ophthalmic Research*, 39: 308-314 (2007).

* cited by examiner

METHOD OF MEASURING ELECTRICAL RESISTANCE VALUE OF CORNEAL TRANS-EPITHELIUM

CROSS-REFERENCE TO RELATED APPLICATIONS(S)

This application is the U.S. national phase of International Patent Application No. PCT/JP2009/053968, filed on Mar. 3, 2009, which claims priority to Japanese Patent Application No. 052567/2008, filed Mar. 3, 2008.

TECHNICAL FIELD

The present invention relates to a method for measuring a corneal transepithelial electric resistance value, which is less invasive to respective tissues of eyes including a corneal epithelium.

BACKGROUND ART

A cornea is a transparent membrane with a thickness of about 0.5 mm, and has a five-layer structure which consists of corneal epithelial cells, a Bowman membrane, corneal stroma, a Descemet's membrane and corneal endothelial cells, in this order from the surface of body. Among these, although the corneal epithelial cells have high regenerating capability, a serious corneal ulcer might occur, or a nonreversible corneal opacity might be left, in the case where a disorder of the epithelial cells is serious. Therefore, there have been strong demands for measuring the degree of the disorder of the corneal epithelium quantitatively and carrying out a proper treatment in an earlier stage.

Since the conventional method for measuring the degree of a disorder of the cornea mainly depends on a visual inspection method, it is difficult to quantitate the disorder of the corneal epithelium, and there has been a demand for a method for representing the degree of the disorder of the cornea by a numeric value and for quantitating the degree of the disorder thereof.

In recent years, it has been known that by measuring a corneal transepithelial electric resistance (TER) that represents a barrier function of the cornea, the degree of the disorder of the cornea can be quantitatively measured (see Non-Patent Documents 1 to 3). The TER is indicated by the product of a corneal electric resistance value (Rc) and an area (a) of a portion to be measured, that is, TER=Rc×a. When the corneal epithelium has a disorder, the barrier function of the cornea is lowered to cause a low corneal TER value. The present inventors at first carried out experiments in which a cut-out cornea was fixed on a Ussing chamber by which an accurate TER can be determined by using a short-circuit current method, with the value of the area (a) being constant; however, since the cut-out cornea is different in its state from that in a living body, the experiments failed to reflect a true biological reaction. Therefore, the present inventors have found a method in which electrode needles are placed on the corneal epithelium and in the anterior chamber of a living eye and an electric resistance is measured by flowing an electric current therebetween (see Non-Patent Document 4). In this case, the measurement of TER is performed for a living cornea by using the principle of the Ussing chamber, and an accurate TER can be determined when the value of the measurement area (a) is constant.

However, since this method is an invasive method that is accompanied by an anterior chamber centesis, it is not possible to apply this method to human, and this method is not suitable for diagnosis and treatment of a corneal disorder in the clinical field.

Non-Patent Document 5 has disclosed a method for measuring a corneal resistance value about a living eye by using corneal contact lens (CL) provided with electrodes. Since this method is not invasive to respective portions of the eye, it may be applicable to human.

However, in this method, since a suitable insulator is not provided, a reliable electric current flow through the corneal epithelium cannot be made because of the existence of a lacrimal fluid on a surface of the eye, and the resulting measured value is considered to mainly represent the state of the lacrimal fluid rather than the state of the corneal epithelium. Moreover, since the CL is fixed onto the cornea by suction, the measuring device itself might cause a corneal disorder. Furthermore, it has been reported in the Japanese Society for Ocular Pharmacology in 2007 that this method failed to detect the existence of small corneal erosion. It can be considered that the electrodes fail to sufficiently detect the corneal disorder, since an electric current to be measured does not completely pass through the corneal epithelium. In addition, since this method does not take the area (a) through which the electric current flows into consideration, a TER that enables accurate evaluation of the corneal disorder cannot be determined. In this manner, the method of Non-Patent document 5 has a problem with the detection sensitivity.

Moreover, Patent Document 1 has disclosed a device for detecting a damage and the like of the corneal epithelium, and this device measures a reduction in a potential difference between a cornea and a sclera as an index for the damage. A corneal electric potential (Vc) serving as a parameter in Patent Document 1 is defined by the corneal electric resistance value (Rc) and an ion transporting function (current) (Ic) by the corneal endothelium, which is represented by Vc=Rc×Ic. Moreover, a corneal electric potential (Vc) is compared with the scleral electric potential (Vs) and k in Vc=kVs serves as an index indicating the corneal disorder. Consequently, k=Rc×Ic/Vs represents the corneal disorder. In this measurement, in order to reflect the Rc to the k, the Ic and the Vs need to be measured with high precision; however, in an actual operation, the current Ic generated from the corneal endothelium is very weak and is not constant. Since the scleral electric potential Vs varies depending on measuring conditions and individuals, it is not possible to determine a corneal disorder accurately when compared with this. Moreover, as described earlier, the TER, which directly reflects the corneal disorder, is represented by TER=Rc×a, and in order to determine a TER, the area (a) through which a current passes needs to be determined; however, it is not accurately determined by this measurement. Consequently, it is not possible to accurately measure the corneal disorder by using this measuring method.

Although Patent Document 1 roughly observes the electrophysiological phenomenon that the electric resistance value is lowered upon occurrence of a corneal disorder, its measuring principle and accuracy are far behind the technique of the present application.

patent document 1: JP-Y-S48-10716
non-patent document 1: Rojanasakul Y. et al., Int. J. Pharm., (66) 131-142 (1990)
non-patent document 2: Rojanasakul Y. et al., Int. J. Pharm., (63)1-16 (1990)
non-patent document 3: Chetoni P. et al., Toxicol In Vitro, (17)497-504 (2003)
non-patent document 4: Uematsu M. et al., Ophthalmic Research, 39, 308-314, 2007 non-patent document 5: Masamichi Fukuda et al., Atarashii Ganka (New Ophthalmology) 24(4):521-525, 2007

DISCLOSURE OF THE INVENTION

Problems to be Solved by the Invention

An object of the present invention is to provide an evaluation method of a corneal disorder that can measure a disorder of a cornea quantitatively and is applicable to living eyes. Specifically, the object is to provide a measuring method for measuring a corneal transepithelial electric resistance value, in which a corneal TER can be measured with superior sensitivity, and which is applicable to the living eyes.

Means to Solve the Problems

The present inventors have found that by placing one of electrodes on the cornea with the other electrode being placed on the conjunctiva, it becomes possible to provide a method that is less invasive to the eyes in comparison with a conventional method that inserts one of the electrodes into the anterior chamber, and also to obtain results of measurements that are equivalent to the conventional method. The technique of the present invention is characterized in that, as in a Ussing Chamber, a constant current (Im) is passed through a predetermined area (a) of the cornea from a measuring device (volt-ohm meter), and a change ($\Delta Vc$) in a corneal electric potential is measured and an electric resistance value Rc is determined, and in this method, this relationship is presented by TER=Rc×a=($\Delta Vc$/Im)×a. In this case, since Im and a are always constant, and since $\Delta Vc$ can be accurately measured, the corneal disorder can be accurately evaluated by using the TER.

Moreover, the present inventors have successfully manufactured a novel measuring device that is suitable to an implementation of the method, which resulted in the completion of the present invention.

That is, the present invention provides:

[1] A method for measuring a corneal transepithelial electric resistance, comprising placing electrodes on a cornea and a conjunctiva;

[2] the method for measuring a corneal transepithelial electric resistance comprising:
(1) a step of placing a first electrode on the cornea and a second electrode on the conjunctiva; and
(2) a step of flowing an electric current between the first electrode and the second electrode to measure an electric resistance;

[3] the method described in [1] or [2], wherein a periphery of the electrode placed on the cornea is insulated;

[4] the method described in any one of [1] to [3] which is carried out about a living eye;

[5] a device for measuring a corneal transepithelial electric resistance about a living eye, which comprises:
(1) a first electrode suitable to be placed on a cornea,
(2) a second electrode suitable to be placed on a conjunctiva, and
(3) an insulator that insulates the first electrode, with the first electrode and the insulator being integrated;

[6] the device described in [5], wherein the first electrode and the insulator are integrated via a conductor;

[7] the device described in [5] or [6], wherein the second electrode is further integrated;

[8] the device described in any one of [5] to [7], wherein the insulator is made of silicone rubber, and the insulator has a contact surface to the cornea having the same curvature as that of the cornea;

[9] the device described in any one of [5] to [8], wherein the second electrode is formed into a sheet shape;

[10] the device described in any one of [5] to [9], wherein the conductor is a gel of hyaluronic acid or atelocollagen, and so on.

Effects of the Invention

Since there is no need of the anterior chamber centesis in the method of measuring a corneal transepithelial electric resistance value of the present invention, an electric resistance value of human corneal epithelial cells can be measured even for living eyes. Moreover, the method of the present invention provides a simpler method which can obtain results of measurements that are equivalent to a method that uses the anterior chamber centesis.

By utilizing the method for measuring a corneal transepithelial electric resistance value of the present invention, it becomes possible to quantitatively detect a corneal disorder of the living eyes, without the necessity of the anterior chamber centesis. It can be used for a diagnosis of corneal disorder so as to utilize the detection data obtained thereby for an early treatment.

The method for measuring a corneal transepithelial electric resistance value of the present invention makes it possible to perform continuous measurements in a short period of time, and is useful for the research for drug screening (for example, pre-clinical studies and the like), the research for evaluating efficacy of drugs, the research for evaluating the corneal toxicity of a drug, and so on.

The method for measuring a corneal transepithelial electric resistance value of the present invention makes it possible to measure a barrier function of a living cornea, which has been impossible by the conventional method. Thus, it becomes possible to obtain useful new findings with respect to corneal barrier functions in various corneal diseases, and consequently to contribute greatly to developments of the ophthalmology and ophthalmic medicine.

EXPLANATION OF SYMBOLS

Figure 1:
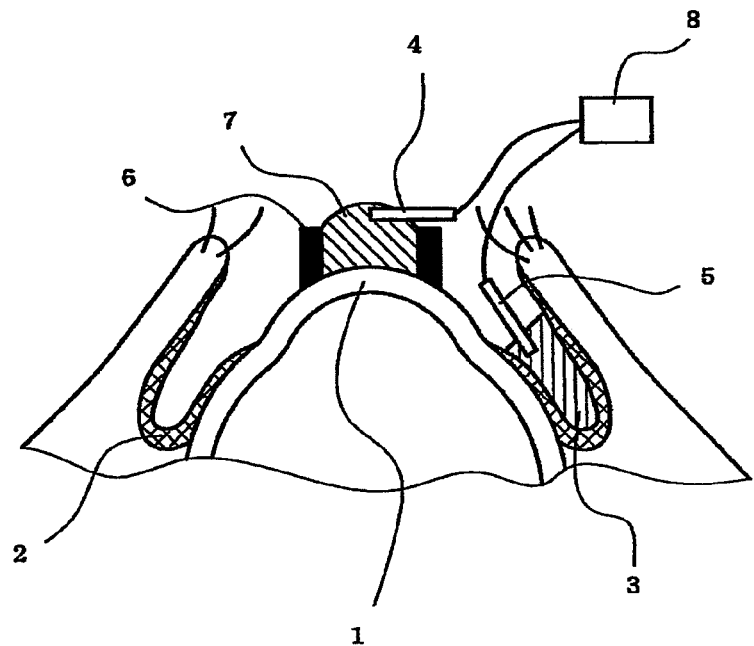
FIG. 1 is a schematic drawing that shows one embodiment of the present invention. A corneal electrode is disposed in a conductor (buffer solution) which fills the inside of an insulator. A conjunctival electrode is in contact with a lacrimal fluid reserved in a conjunctival-sac.

1 cornea
2 conjunctiva
3 lacrimal fluid reserved in conjunctival-sac
4 corneal electrode
5 conjunctival electrode
6 insulator
7 conductor
8 electric resistance value measuring device
9 conjunctival electrode portion

BEST MODE FOR CARRYING OUT THE INVENTION

The present invention provides a method for measuring a corneal transepithelial electric resistance, comprising placing electrodes on a cornea and a conjunctiva (referred to as the method of the present invention).

More specifically, the method of the present invention comprises:
(1) a step of placing a first electrode (referred to also as a corneal electrode) on the cornea and a second electrode (referred to also as a conjunctival electrode) on the conjunctiva; and
(2) a step of flowing an electric current between the first electrode and the second electrode to measure an electric resistance.

In the present specification, "corneal transepithelial electric resistance" means "transepithelial electric resistance: TER" of "cornea".

It is considered that the TER reflects the barrier function of the epithelium. It has been known that as the measured TER is lower, the disorder degree of the epithelial cell is higher. That is, by measuring a corneal transepithelial electric resistance, the barrier function of the corneal epithelium can be evaluated so that the disorder degree of the corneal epithelial cell can also be evaluated. The "barrier function" means a function of controlling various substances that move into and out of the body through the epithelium, which is acquired by the forming of junctions peculiar to the epithelial cell, such as an occluding junction (tight junction) and an anchoring junction (adherens junction, desmosome, and the like) among the epithelial cells.

In the case of a normal cornea without any disorder, the value of the corneal transepithelial electric resistance of, for example, is about 100 to 700 $\Omega \cdot cm^2$ for rabbit, when measured by using a conventional method with an isolated corneal piece (cut-out corneal piece). In the case where the method of the present invention is used, since there is less corneal epithelium disorder due to a cut-out of the corneal piece, a TER value that is slightly higher than this can be obtained. Specifically, in the case where the measuring is carried out by the method of the present invention, the normal value of the corneal transepithelial electric resistance of the rabbit is about 500 to 1500 $\Omega \cdot cm^2$.

The reduction of the corneal transepithelial electric resistance (corneal TER) value serving as an index of a degree of disorder of the cornea is considered to be a result of a rise of the substance permeability of the cornea due to a disorder (referred to also as an injury) of the corneal epithelial cells, that is, a reduction of the barrier function.

Since the corneal epithelium is located at the outermost portion of the cornea and contacts with the outer environment, it is a portion that is easily subjected to a disorder. In the present specification, the disorder of the cornea, the disorder of the corneal epithelium and the disorder of the corneal epithelial cells are terms that are used interchangeably. The disorders of the corneal epithelial cells refer to as various disorders causing damages to junctions, such as an occluding junction (tight junction) and an anchoring junction (adherens junction, desmosome, and the like) among the corneal epithelial cells, and for example, the disorders include a corneal erosion, a corneal ulcer, a corneal perforation, a corneal edema (epithelial edema), a corneal infection (bacterial corneal ulcer, keratomycosis, viral keratitis, and so on). These disorders of the corneal epithelial cells may be caused by a trauma, an inflammatory reaction, ultraviolet rays, hypoxia, dry eyes, improper wear of contact lens, foreign substances such as dusts, chemicals and agents (for example, an antiseptic contained in eye drops) and the like. The disorders of the corneal epithelial cells may lead microorganism infection into the eyes, an ulcer, low vision and the like.

The corneal epithelial cells can be regenerated; however, when there is a serious disorder to the corneal epithelial cells, it will affect adversely a group of cells inside thereof (collectively referred to as corneal endothelial cells in the present specification). Since the regenerating capability of the corneal endothelial cells is lower than that of the corneal epithelial cells, the disorder of the corneal epithelial cells is preferably treated in an earlier stage. For this purpose, it is preferable that the disorder of the corneal epithelial cells needs to be detected earlier.

Additionally, in the following examples, the corneal disorder is induced by using benzalkonium chloride (BAC) generally used as an antiseptic in eye drops and the like; however, it is clear that the method of the present invention can be applicable to a detection of any corneal disorder caused by any of the above-mentioned reasons.

When used in the present specification, "the degree of disorder of the cornea" means a degree of disorder of the corneal epithelium, and it is represented qualitatively as a percentage % of a TER value after subjected to a corneal disorder relative to the normal value without any corneal disorder.

In the measuring method for the corneal transepithelial electric resistance of the present invention, electrodes to be used for the measurements are respectively placed on the cornea and on the conjunctiva.

The conjunctiva is composed of a bulbar-conjunctiva, a conjunctival formices and a palpebral-conjunctiva. In the present invention, "the conjunctiva" includes any of membranes forming the conjunctiva. Moreover, in the present specification, a space formed by these conjunctiva (a sac-like structure of conjunctiva centered on the conjunctival formices) is referred to as "the conjunctival-sac".

In the present specification, the expression "placing an electrode on the cornea" means that an electrode is disposed at a position in contact with the outer surface of the corneal epithelium directly or indirectly via a conductor. Moreover, the expression "placing an electrode on the conjunctiva" means that the electrode is disposed in the conjunctival-sac at a position in contact with the outer surface of the bulbar-conjunctiva, conjunctival formices or palpebral-conjunctiva, or at a position in contact with any of the above conjunctivas via a conductor.

Electrodes to be placed on the cornea and the conjunctiva can be a positive electrode or a negative electrode so long as at least one positive electrode and at least one negative electrode are placed on the cornea and the conjunctiva, respectively. The number of the electrodes to be used is not particularly limited, and the number may be determined by the person skilled in the art as necessary.

The kinds of electrodes to be used are not particularly limited as long as the objective and effects of the present invention can be achieved, and any electrodes known per se for measuring the transepithelial electric resistance may be utilized as necessary.

For example, materials for the electrode include gold, platinum, silver, silver chloride, copper, stainless steel, iron, carbon and the like. Preferably, the electrode of gold, platinum, silver, or silver chloride is used from a viewpoint of being less harmful to a living body.

Although the form of the electrodes is not particularly limited, any electrodes known per se used for the living body may be used as necessary, as long as the objective and effect of the present invention can be achieved without giving any disorder to the tissue of the eyes. For example, electrodes having various shapes, such as a rod shape, a plate shape, a disc shape and a ring shape, made of the above-mentioned electrode materials, may be proposed without limitation. The electrode may be directly contacted with the cornea or the conjunctiva without a conductor, or may be used together with the conductor.

The conductor is placed at a gap portion between the electrode and the cornea or the conjunctiva. Although not particularly limited as long as the objective and effect of the present invention can be achieved without giving any adverse effect to the eyes, any materials known per se as a conductor material may be used as necessary. The conductor may be solid, liquid, gel and the like, and from the viewpoint of closely contacting the electrode more flexibly with the cornea and/or conjunctiva, liquid or gel is preferably used. In this case, the conductor includes physiological saline, buffer solution (for example, a phosphate buffer solution, Hanks' Balanced Salt Solution, and the like) and hydrogel (for example, a gel of hyaluronic acid or atelocollagen, and the like), but not limited thereto. In the case of the conjunctival electrode, the conductor may be substituted with a lacrimal fluid reserved in the conjunctival-sac. In the case where a solid-state conductor is used, the contact surface to the cornea or conjunctiva of the conductor is desirably formed into a shape adapted to the shape of the outer surface of the cornea or the conjunctiva so as to be contacted with the cornea or the conjunctiva as closely as possible (for example, when used for the corneal electrode, the contact surface to the cornea has the same curvature as that of the cornea).

Because the measuring method of the present invention measures corneal transepithelial electric resistance by flowing an electric current through the corneal epithelium, the electric current needs to surely pass through the corneal epithelium. Since a lacrimal fluid normally exists on the cornea, the electric current flows through not only the corneal epithelium, but also the lacrimal fluid, in the case where the electrode is simply placed on the cornea, with the result that there is a possibility of a failure to obtain a accurate corneal transepithelial electric resistance value.

Therefore, in order to flow the electric current between the electrodes to surely pass through the corneal epithelium and to prevent the short circuit of the electric current through the lacrimal fluid and the like, an insulator is preferably disposed around a periphery of the cornea electrode (in the case where a conductor is interposed between the electrode and the cornea, around a periphery of the conductor). As materials for the insulator, not particularly limited, any substance known per se may be used as an insulating substance as necessary, as long as it can achieve the objective and effect of the present invention without giving any adverse effect to the eyes, and a nitrile rubber, a silicone rubber, such as polydimethylsiloxane (PDMS), and the like may be proposed without limitation. A plurality of insulators may be combined, and used as necessary.

In a preferred embodiment, the insulator is provided in a form integrated with the corneal electrode. The expression that the insulator and the corneal electrode are "integrated" means that the insulator and the corneal electrode are pre-arranged in such a manner that the placement of the insulator and the placement of the corneal electrode need not be carried out separately, and examples of such arrangements include an arrangement in which the insulator and the corneal electrode are directly contacted with each other to form an integrated shape, and an arrangement in which another substance, such as a conductor, is interposed between the insulator and the corneal electrode to form an integrated shape as a whole, but not limited thereto.

The shape of the insulator may vary depending on the shapes of the electrode, the conductor and the like to be used; however, the shape is not particularly limited, as long as it is placed around the periphery of the electrode or the conductor so as to prevent the short circuit of the electric current from the electrode or the conductor to the lacrimal fluid and the like, and has a shape capable of closely contacting with the cornea. For example, as the shape of the insulator, a ring shape, a cylindrical shape and the like are proposed. Moreover, it is also proposed to set the corneal contact surface of the insulator to have the same curvature as that of the cornea for the close contact with the cornea.

For example, in the case where a ring made from nitrile rubber is used as the insulator, a dimension of the ring may be selected as necessary within a range in which its diameter (at least an inner diameter) does not exceed a diameter of the cornea. For example, in the case of human, an inner diameter of the ring is preferably 3 to 9 mm (for example, about 6 mm). In the case of rabbit, for example, an inner diameter of the ring is 3 to 11 mm (for example, about 7 mm).

In order to insulate the corneal electrode from the conjunctival electrode, it is desirable to closely contact the insulator with the cornea upon contacting it with the cornea. Methods for closely contacting the insulator thereto include a method using a light pressing, a suction by a negative pressure, an insulator gel, adhesive, eye ointment, etc., and those that give no damages or disorders to the cornea and the other eye tissues are preferably used. Specifically, for example, the method using a light pressing, the insulator gel or eye ointment is preferably used, and the insulator gel and the eye ointment are particularly preferable. As the insulator gel, although not particularly limited, petrolatum and the like may be used. As the adhesive, cyanoacrylate type adhesive, acrylic resin type adhesive and the like are proposed, without limitation. As the eye ointment, Tarivid eye ointment (registered trademark), Flavitan ophthalmic ointment (registered trademark) and so on are proposed, without limitation.

In the present invention, the electric current to be flowed between the electrodes is not particularly limited, as long as the TER value can be measured without causing any damage to the epithelial cells, and it is preferably 10 µA to 10 mA, more preferably 20 µA to 100 µA. The electric current may be either a DC current or an AC current.

The TER value can be obtained by measuring a change in voltage depending on an electric current, and calculating a resistance value by Ohm's law (voltage=current×resistance). As a measuring device for measuring an electric resistance, a short-circuit current device, a voltage-electric resistance value measuring device (for example, EVOM (registered trademark, from World Precision Instruments, Inc.)) and the like may be used, without limitation.

The TER value is expressed by $\Omega \cdot cm^2$, and obtained by multiplying the resulting electric resistance value by an area (a) where the current is passed through. The area (a) corresponds to an area of the cornea inside the insulator that is placed around the corneal electrode. By comparing this value with a normal value, and the like, it is possible to quantitatively evaluate the degree of disorder of the corneal epithelial cells.

Since the method of the present invention is less invasive, it is applicable to a living eye. In the present invention, the expression "living eye" means an eye that has not been taken out of the living animals exemplified below as the subject for the application of the present invention. The living eye means an eye that has not been subjected to an invasive operation, such as an extraction, incision, and the like.

Examples of the subject for the application of the method of the present invention include: mammals such as human, experimental animals, pet animals and domestic animals (for example, rabbits, rats, mice, hamsters, cats, dogs, cows, swine, horses, sheep, monkeys, and the like). Among these, the method of the present invention is intended to be applied to those experimental animals for use in the preclinical study of eyedrop and the like and animals whose treatment for corneal disorder is desired. The mammal is preferably human.

The present invention also provides a device for measuring a corneal transepithelial electric resistance of a living eye (referred to as the device of the present invention), and this device comprises (1) a first electrode suitable to be placed on a cornea, (2) a second electrode suitable to be placed on a conjunctiva, and (3) an insulator that is integrated with the first electrode. The respective components of this device are as above-mentioned.

As the first electrode, the corneal electrode, described in detail in the above-mentioned method of the present invention, is preferably used. As the second electrode, the conjunctival electrode, described in detail in the above-mentioned method of the present invention, is preferably used. Furthermore, as the insulator, the aforementioned insulator described in detail in the method of the present invention, is preferably used. The device of the present invention is characterized in that the corneal electrode and the insulator are integrated. In this case, the expression "integrated" is used as the same meaning as that explained before. The integrated corneal electrode and the insulator, is hereinafter referred to as a "corneal electrode portion". In the case where the electrode is designed to be directly contacted with the cornea, the corneal electrode portion may consist of only the electrode and the insulator, or may further include a member for connecting the electrode with the cornea. On the other hand, in the case where the electrode does not directly contact with the cornea, the corneal electrode portion may further include a conductor for contacting the electrode indirectly with the cornea as another component. That is, in a preferred embodiment, the corneal electrode portion has a corneal electrode integrated with the insulator via the conductor. In this case, as the conductor, a solid or gel-like material may be selected for maintaining integrity of the corneal electrode portion. Considering a shape stability before use and the close contact to the cornea during use, a material, such as hydrogel (for example, a gel of hyaluronic acid, atelocollagen, and the like), is particularly preferable.

The shape of the corneal electrode itself is not particularly limited, as long as it can be kept inside the insulator around the corneal electrode, and any electrode known per se as an electrode for measuring a transepithelial electric resistance, and the like, may be used as necessary. For example, various shapes, such as a rod shape, a plate shape, a linear shape and the like, are proposed, although not intended to be limited thereto. Any shape may be used as a shape of the corneal electrode portion, as long as it can make close contact with the cornea, and specific examples thereof include a circular cylinder shape, a rectangular cylinder shape, and the like, with a concave portion as a contact surface to the cornea; however, not particularly limited thereto; as a shape of the corneal electrode portion, for example, an applanation tonometer-like shape and a contact lens-like shape may also be used.

The size of the corneal electrode portion may be of any size as long as an inner diameter of the insulator does not exceed a diameter of the cornea, and in the case of human, an inner diameter of the insulator is preferably up to the corneal diameter (about 12 mm), and preferably 1-12 mm.

An electrode alone may form a conjunctival electrode, or a conjunctival electrode and a solid or gel-like conductor may be integrated (inclusively referred to as a "conjunctival electrode portion"). The size of the conjunctival electrode portion may be a size that the entire conjunctival electrode portion can be kept in the conjunctival-sac; however, it is sufficient that at least one portion of the conjunctival electrode portion can be made in contact with the conjunctiva or a lacrimal fluid reserved in the conjunctival-sac. Taking into consideration the size of the entire conjunctival electrode portion to be kept in the conjunctival-sac, the size is preferably within a range of 1-10 mm as a whole, in the case of human. A shape thereof may be any shape as long as it allows the conjunctival electrode portion to be contacted with a conjunctiva or a lacrimal fluid reserved in a conjunctival-sac, and preferably, a shape without giving disorders to the tissues of the eyes. Specifically, examples thereof include, but not limited to, a flat shape, a plate shape, a linear shape, a sheet shape, and the like, with its conjunctival contact surface being concave. Further, in one preferred embodiment, the corneal electrode portion and the conjunctival electrode portion are integrated in such a mode as to prevent an electric current from flowing directly therebetween.

Figure 2:
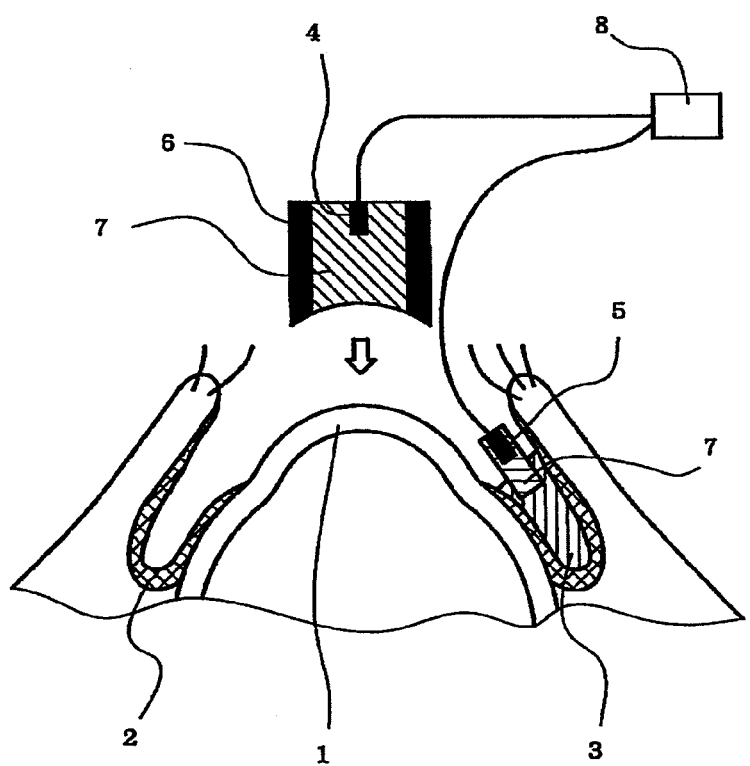
FIG. 2 is a schematic drawing that shows another embodiment of the present invention. A corneal electrode of an applanation tonometer type (with conductor (gel) inside an insulator) is used, and a conjunctival electrode is covered with the conductor (gel).
Figure 3:
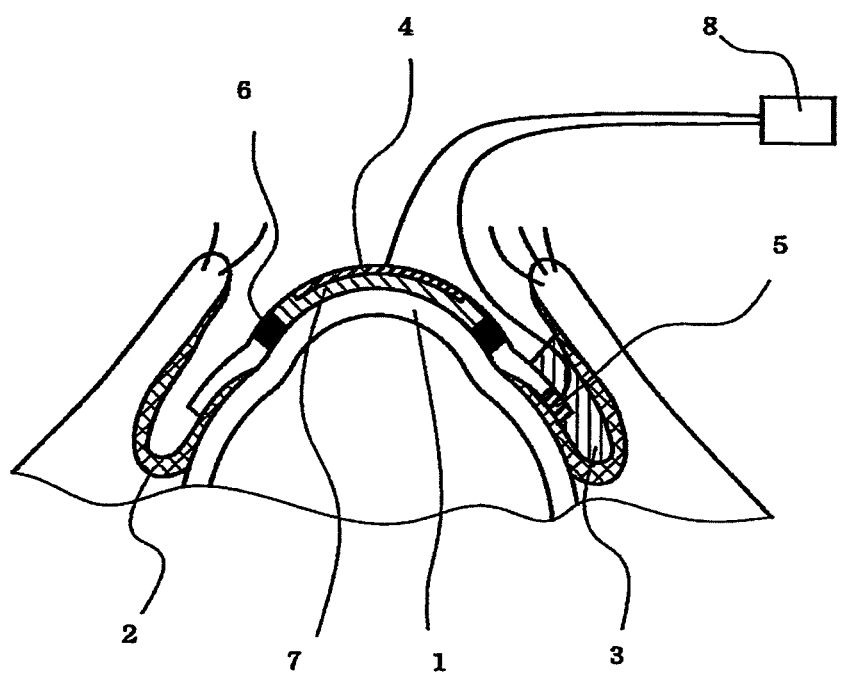
FIG. 3 is a schematic drawing that shows still another embodiment of the present invention. An electrode of a contact lens type, which is equipped with a corneal electrode, a conductor (gel), an insulator and a conjunctival electrode, is used.

FIGS. 1 to 3 are schematic drawings (sagittal plane) that exemplify possible embodiments of the present invention. However, illustrated embodiments are exemplary only. FIG. 1 shows an example of a corneal electrode that uses a ring-shaped insulator and a buffer solution. FIG. 2 shows an example of a corneal electrode of an applanation tonometer type, and FIG. 3 shows an example of a contact lens-type electrode. In FIG. 3, the conjunctival electrode is attached to an edge portion of a contact lens.

In the case where the electrode is formed into a contact-lens shape, any material generally used for the contact lens may be used as the material constituting the external portion of the insulator, and for example, plastic materials (for example, acrylic resin, polycarbonate, and the like), rubbers and the like may be used, although not particularly limited thereto.

Figure 6:
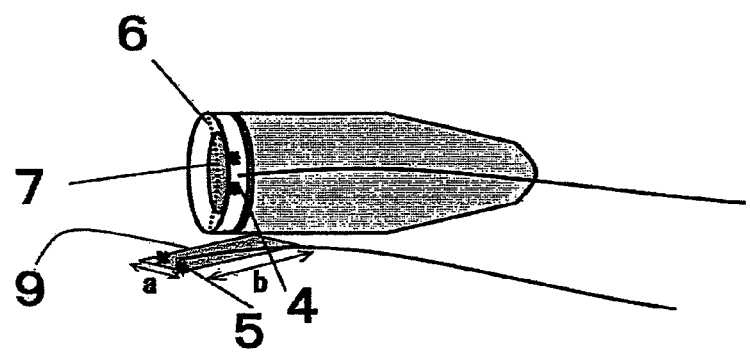
FIG. 6 is a schematic drawing that shows a particularly preferable TER measuring device of the present invention. A corneal contact surface of an insulator has a curvature that is the same as that of the cornea and a conjunctival electrode portion is formed into a sheet shape.

FIG. 6 is a schematic drawing that shows one example of a particularly preferred embodiment of the present invention.

In this embodiment, since the corneal electrode, the insulator, the conductor and the conjunctival electrode are integrated, immediate measurement of TER is readily possible only by contacting this system with the living eyes, which consequently eliminates time-consuming setting processes; thus, it presents to the reduction of stress on a subject.

In the present embodiment, silicone rubber, nitrile rubber and the like may be used as the insulator. Examples of the silicone rubber include: polydimethylsiloxane (PDMS), vinyl methyl silicone rubber and the like may be proposed, without limitation. The silicone rubber is particularly preferable as a highly safe material because of its high biocompatibility and softness, which causes scratches on the corneal surface, and further it is an easily processible material. By using the silicone rubber as the insulator, it is possible to prevent corneal abrasion caused by the measuring device.

The insulator is preferably a ring shape or a cylindrical shape (for example, inner diameter: 1 to 13 mm (for example, 3 to 11 mm), thickness: 0.1 to 5 mm (for example, 1 to 3 mm), and height: 0.1 to 20 mm (for example, 1 to 10 mm)), and its contact surface to the cornea has the same curvature as that of the cornea. In this case, the expression "the same curvature as that of the cornea" means that the contact surface has the same curvature or substantially the same curvature as that of the cornea, as long as the close contact between the insulator and the cornea is ensured, that is, the contact surface does not necessarily have the perfectly same curvature as that of the cornea. The thickness at the contact surface may be greater than the above-mentioned thickness.

The curvature of the cornea can be measured by a general method using an ophthalmometer, a keratometer, a photokeratoscope, and the like, and the curvature to be applied to the insulator may be altered depending on kinds and the like of a subject as necessary. For example, in the case of human, the curvature radius is 650 to 850 mm (for example, 790 mm). In the case of rabbit, the curvature radius is 600 to 800 mm (for example, 750 mm).

In order to accurately measure the TER, steady insulation is required between the electrodes. In particular, since the eye surface is covered with the lacrimal fluid, it is not possible to measure the TER accurately in the case where an insufficient insulation allows an electric current passing through the lacrimal fluid. Preferably, the entire peripheral portion of the insulator is surely contacted with the cornea by a light pressing and the like so as not to leave any lacrimal layer between the insulator and the eye surface. The insulator is desirably made to have a certain thickness (preferably, 1 to 3 mm) so that, even when the lacrimal fluid layer is left, only less electric current can pass through the lacrimal fluid layer, that is, the value of electric resistance over the lacrimal fluid layer becomes greater so that the value of electric resistance over the epithelium can be ignored. Any insulating method may be used as long as the insulation is positively achieved.

A conductor gel is disposed inside this insulator (for example, see FIGS. 2 and 6). As the conductor gel, for example, gels of synthetic macromolecules, such as polyethylene glycol containing a buffer solution, and gels of biological macromolecules, such as hyaluronic acid, atelocollagen, gelatin, cellulose and agarose, may be used. It is preferable to use the gel of hyaluronic acid and atelocollagen, because they are superior in biocompatibility and highly safe materials with a conductive property, and easily processed; however, a material of the gel is not limited thereto, as long as it meets these conditions. As in the case of insulator, it is also preferable that the corneal contact surface of the conductor gel has the same curvature as that of the cornea, in order to be closely contacted with the cornea.

Preferably, the corneal electrode is disposed so as to be contacted with the conductor gel, or embedded into the conductor gel so that the corneal electrode and the insulator can be integrated (corneal electrode portion). As a result, the corneal electrode is indirectly contacted with the cornea via the conductor gel. The corneal electrode to be used is miniaturized one adapted to the present embodiment. The size/shape/material and the like of the corneal electrode are the same as those described earlier.

Further, an outside shape of a portion including the corneal electrode portion, as a whole, is not particularly limited, and may be altered as necessary depending on modes of use, and determined appropriately by taking into consideration, for example, easiness in handling, installation into a usual ophthalmology medical device (such as a slit-lamp and an ophathalmotonometry receptacle), and the like; as an example, a shape as shown in FIG. 6 is proposed. For example, the outside shape of the portion including the corneal electrode portion, as a whole, may be formed into a shape that can be grabbed by the hand and operated (for example, a pen shape), without limitation.

The above-mentioned insulator itself may constitutes the outer layer that forms the outer shape, or the corneal electrode portion (in this context, with the conductor also included) may be integrated with another member that forms the outside shape as above.

Moreover, in the present embodiment, the conjunctival electrode portion is formed into a sheet shape. The sheet shape means a shape having, for example, a thickness in a range from 0.001 cm to 0.1 cm, a length (b in FIG. 6) in a range from 0.5 cm to 5 cm, and a width (a in FIG. 6) in a range from 0.1 cm to 2 cm, and a preferable example is a sheet having a thickness of 0.01 cm, a length of 1 cm and a width of 0.5 cm. A sheet having any shape, such as a rectangular shape, a round shape, and an elliptical shape, may be used; however, a sheet having an approximately rectangular shape is preferably used. In order to prevent abrasion upon contact with the conjunctiva, a shape with rounded corners may be also used. By forming the conjunctival electrode into a sheet shape, its insertion into the conjunctival-sac can be easily carried out.

This sheet can be made from, for example, a material, such as PET, polyimide, silicone rubber and acrylic material, and, from viewpoints of high strength, high flexibility and easiness in molding, PET and polyimide are preferably used.

The conjunctival electrode is preferably disposed at a distal end (on an opposite side to the attachment point to the corneal electrode portion) of the sheet-shaped conjunctival electrode portion; however, it may be disposed at any position, as long as the direct contact with the conjunctiva or the lacrimal fluid reserved in the conjunctival-sac, or the indirect contact therewith via a conductor can be ensured, and for example, it may be disposed at a position within 5 mm from the distal end of the conjunctival electrode portion. The conjunctival electrode portion may be formed into a shape covered with a conductor, wherein the aforementioned hydrogel may be used as the conductor, however, not particularly limited to this, any gel may be used as long as it has a conductive property. The conjunctival electrode is preferably disposed on the conjunctival contact side of the sheet; however, in the case where the conductor is used, it may be disposed on the outer side (on the side opposite to the conjunctival contact surface) of the sheet, or may be embedded into the conductor.

Upon measurements, the conjunctival electrode is held on the conjunctiva, or inside the conjunctival-sac, or inside the lacrimal fluid, and the position is at 0.1 to 15 mm from the corneal limbus, and is desirably at 3 mm therefrom.

The conjunctival electrode portion is attached to the corneal electrode portion with an angle according to a shape of the eyeball, so as to be appropriately placed when the present device is contacted with the conjunctiva.

The corneal electrode portion and the conjunctival electrode portion may be altered as necessary depending on the sizes of the cornea and eyeball of the subject. For example, in the case of human infant, human child, mouse, rat, monkey and so on, the size may be made smaller, while in the case of large-size animals, such as swine and cow, the size may be made larger.

The present invention further provides a drug screening system which is characterized in that the above-mentioned method of the present invention is used, or in that the device of the present invention is involved as a component. Since the application of the method of the present invention and the device of the present invention makes it possible to quantitatively measure a corneal disorder of the living eyes, it is possible to carry out a screening for candidate compounds of a therapeutic agent for diseases causing disorders to the cornea (such as, for example, corneal erosion, a corneal ulcer, a corneal perforation, a corneal edema (epithelial edema) and a corneal infection (such as bacterial-corneal ulcer, keratomycosis, viral keratitis and the like)) by using the model animal with an induced corneal disorder. That is, in the model animal, before and after the administration of a test compound, TER measurements are carried out about the living cornea, and those test compounds whose administrations have significantly improved the TER value can be selected as candidate compounds for the therapeutic agent of the disease causing the disorder of the cornea.

The present invention further provides an efficacy and/or toxicity evaluation system for drugs which is characterized in that the above-mentioned method of the present invention is used, or in that the device of the present invention is involved as a component. Since the application of the method and device of the present invention and the device of the present invention makes it possible to quantitatively measure the corneal disorder of the living eye, it is possible to evaluate an efficacy of a therapeutic agent for diseases causing disorders to the corneal (such as, for example, corneal erosion, a corneal ulcer, a corneal perforation, a corneal edema (epithelial edema) and a corneal infection (such as bacterial corneal ulcer, keratomycosis, viral keratitis and the like)), for example, by using an experimental animal with a corneal disorder or a human who is suffering from a disease causing a corneal disorder, as a subject. That is, in the subject, before and after the administration of a drug to be evaluated, TER measurements are carried out about the living cornea of the subject, and in the case where the TER value is significantly improved by the administration of the drug, it is possible to determine that the drug is effective for treatment of the disease causing the disorder of the cornea. On the other hand, for example, by using an experimental animal or a human that is suffering from a disease of the eye other than the corneal disorder as a subject, it is possible to evaluate toxicity to the cornea of a therapeutic agent for the disease. That is, before and after the administration of a drug to be evaluated, TER measurements are carried out about the living cornea of the subject, and in the case where the TER value is significantly worsened by the administration of the drug, it is possible to determine that the drug has toxicity to the cornea.

The present invention also provides a diagnosis agent for a disease causing a disorder of the cornea (for example, corneal erosion, a corneal ulcer, a corneal perforation, a corneal edema (epithelial edema) and a corneal infection (such as bacterial corneal ulcer, keratomycosis, viral keratitis and the like)) that contains a pharmaceutically acceptable substance that can be used as a conductor or used for closely contacting an insulator with the cornea in the method of the present invention. Examples of the pharmaceutically acceptable substance that can be used as a conductor include: physiological saline, a buffer solution (for example, a phosphate buffer solution and Hanks' Balanced Salt Solution and the like), as well as hydrogel and so on. Examples of the pharmaceutically acceptable substance that can be used for closely contacting an insulator with the cornea include an insulator gel, an adhesive, and an eye ointment. Specifically, as the insulator gel, petrolatum and the like may be used, as the adhesive, cyanoacrylate-type adhesive, acrylic resin-type adhesive and the like may be used, and as the eye ointment, Tarivid eye ointment (registered trademark), Flavitan ophthalmic ointment (registered trademark) and so on are proposed, without limitation. The diagnosis agent of the present invention may further contain the other pharmaceutically acceptable additives, such as an antiseptic, an isotonizing agent, a pH adjusting agent and a stabilizer.

The diagnosis of a disease causing a corneal disorder by the use of the diagnosis agent of the present invention is performed by carrying out the above mentioned method of the present invention with the diagnosis agent used as a means for closely contacting the conductor or the insulator with the cornea to measure TER about the living cornea of the subject, and then by comparing the measured value with a normal value.

The following examples will illustrate the present invention in detail; however, the present invention is not intended to be limited by these specific examples.

EXAMPLES

Comparative Example 1

Evaluation of Corneal Disorder Due to BAC by Living Corneal TER Measurement Using Anterior Chamber Centesis (Referred to as "Anterior Chamber Centesis Method")

In accordance with the method described in non-Patent Document 4 supra, electrodes were placed on a cornea and into an anterior chamber of a rabbit, and after administration of 0.02% BAC, a corneal TER was measured.

Example 1

Evaluation of Corneal Disorder Due to BAC by Living Corneal TER Measurement Requiring No Anterior Chamber Centesis (Referred to as Conjunctival Sac Method) (FIG. 1)

Silver-silver chloride electrode having a rod shape was placed on a cornea and into a conjunctival sac of a living rabbit, and a 0.02% BAC was administered thereto. A change in the corneal TER due to exposure to BAC was measured by a voltage-electric resistance value measuring device. A rubber ring (6 mm in the inner diameter) was fixed onto the cornea around the periphery of the electrode by using a bioadhesive (Aron alpha A from Sankyo Co., Ltd.) for insulation, so that an electric current is surely passed through the epithelium of the cornea. An AC current of ±20 μA was flowed, and a change curve of TER, a reduction of TER and a TER value after a lapse of 60 seconds from the exposure to 0.02% BAC, were compared with those from the conventional measuring method in which the anterior chamber centesis was carried out (comparative example 1). The TER value was calculated by subtracting an electric resistance value between the anterior chamber and the conjunctival sac obtained in a preliminary experiment from the measured value.

Figure 4:
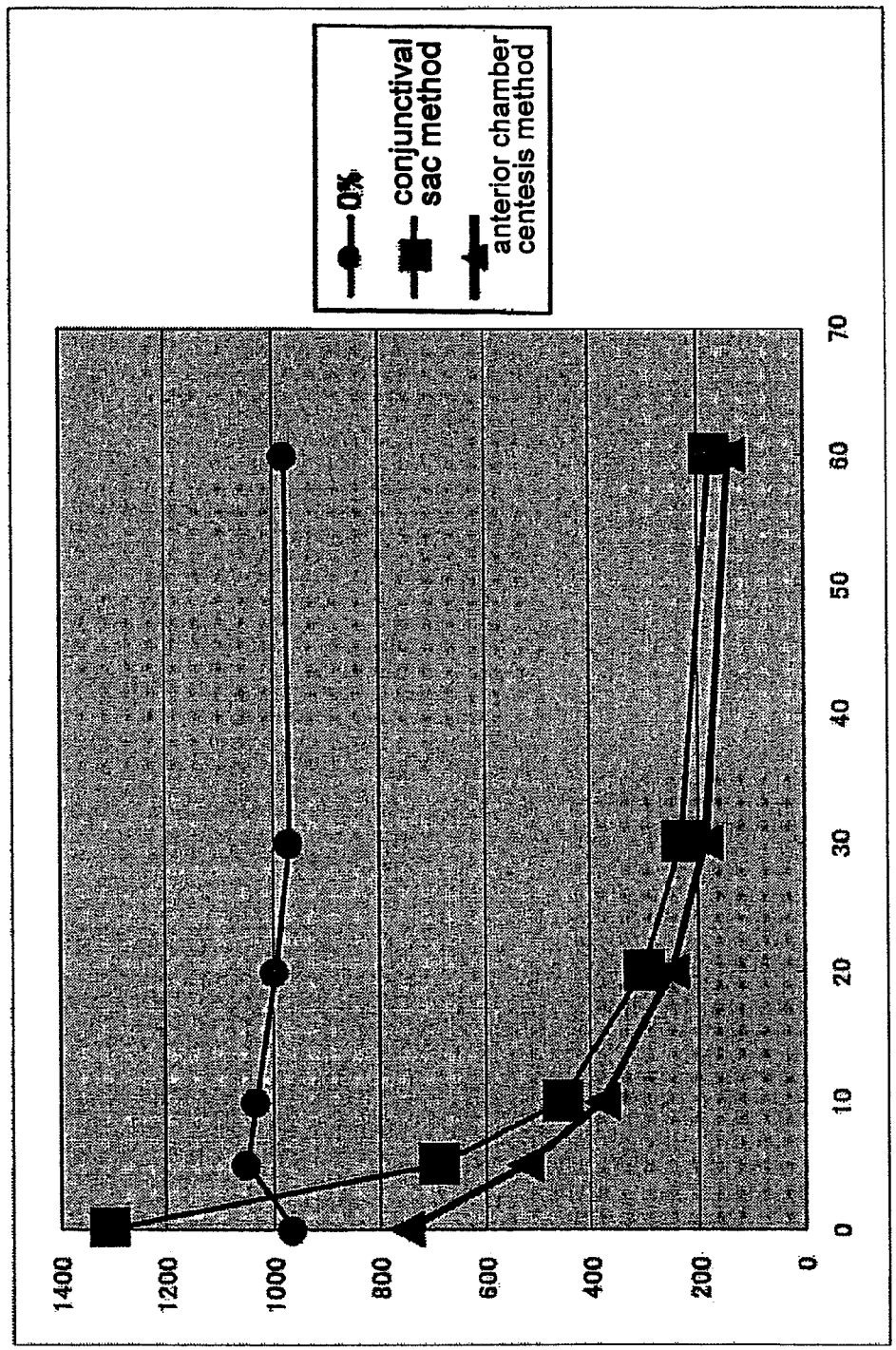
FIG. 4 is a graph that shows measured values of TER after administration of a 0.02% BAC. In the Figure, the axis of ordinates shows $\Omega \cdot cm^2$ and the axis of abscissas indicates seconds that have been elapsed after the administration of the BAC.
Figure 5:
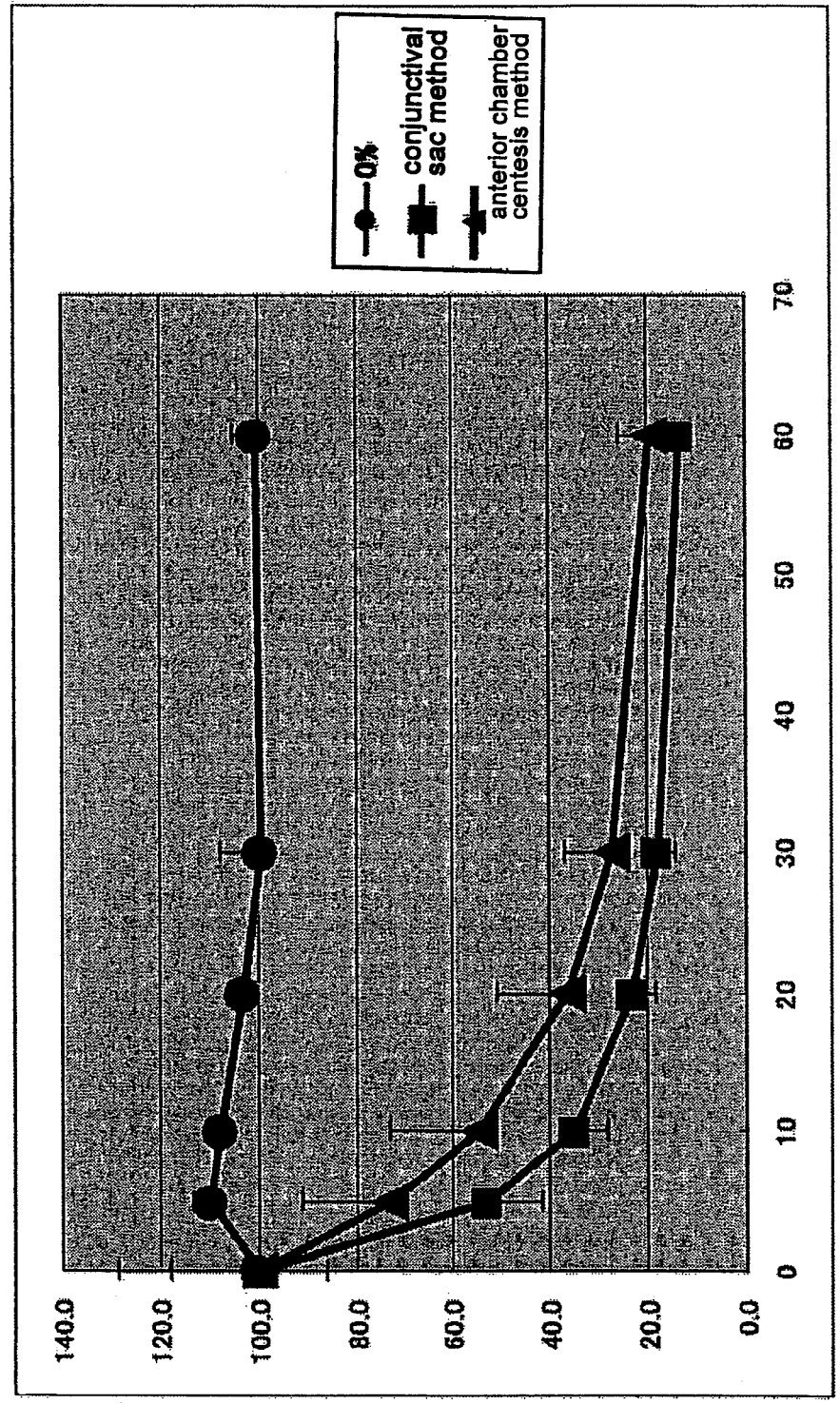
FIG. 5 shows the results of the same measurements as of FIG. 4, when the measured TER value prior to the administration is 100%. In the Figure, the axis of ordinates indicates % and the axis of abscissas indicates seconds that have been elapsed after the administration of the BAC.

FIGS. 4 and 5 show the comparisons of results obtained from comparative example 1 and example 1. When 0.02% BAC was administered, the TER reduction curve obtained by the conjunctival-sac method was similar to the TER reduction curve obtained by the conventional anterior chamber centesis method. Setting the TER before the administration of the BAC to 100%, the TER at ten seconds after the administration was 35.1±6.8%, and after a lapse of 60 seconds, it was significantly reduced to 13.5±2.1% (p<0.01). In the anterior chamber centesis method, 60 seconds after the administration, the TER was 19.7±5.9%. The TER value after a lapse of 60 seconds was 175±14 $\Omega cm^2$ in the conjunctival-sac method, and 138±10 $\Omega cm^2$ in the anterior chamber centesis method.

As described above, it is clear that the method of the present invention (conjunctival-sac method) makes it possible to obtain detection results comparable to those of the anterior chamber centesis method.

Example 2

Preparation of Living Corneal TER Measuring Device (FIG. 6)

Corneal Electrode Portion

A silver electrode and a silver-silver chloride electrode having a diameter of 1 mm were placed on a round cover glass having a diameter of 12 mm. PDMS having a circular cylinder shape with 10 mm in diameter and 6 mm in inner diameter and having a curvature radius of the corneal contact surface of 7.9 mm was secured onto the cover glass by using an adhesive. An Eppendorf tube was attached to a rear side (on the side opposite to the corneal contact surface (cover glass side)) for mount onto a slit-lamp. The inner space of the PDMS was filled with an atelocollagen gel and its curvature radius was adjusted to 7.9 mm.

Conjunctival Electrode Portion

A silver electrode and a silver chloride electrode having a diameter of 1 mm were placed on a PET sheet of 0.005×0.5×1 cm, at position of 1 mm from the distal end of the sheet on the eyeball side. The PET sheet, the silver electrode and the silver chloride electrode were thinly coated with a collagen gel. This conjunctival electrode portion was secured to the Eppendorf tube of the corneal electrode portion with an angle according to a shape of the eyeball by using an adhesive.

TER Measurements

By using thus prepared TER measuring device, a change in the corneal TER of a living rabbit was measured. A Japanese white rabbit was put under general anesthesia and the eyes were kept open by using adhesive tapes. The above-mentioned device is attached to the tip of the slit-lamp, the corneal electrode portion was correctly contacted with a center portion of the cornea and the conjunctival electrode portion was contacted with the conjunctival-sac and the lacrimal fluid reserved therein, by operating the slit-lamp.

Figure 7:
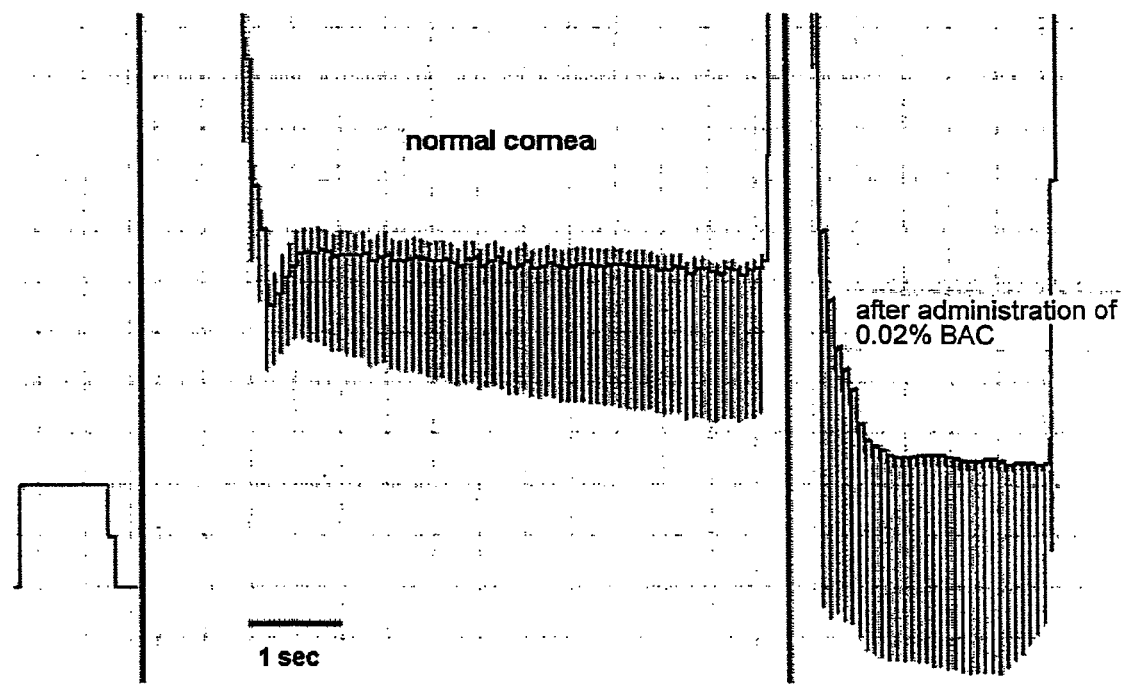
FIG. 7 shows a record of TER of a normal cornea before and after the administration of a 0.02% BAC to the cornea, measured by the measuring device of FIG. 6. The TER value became a stable value within 1 second, after the measuring device had been contacted with the cornea.
Figure 8:
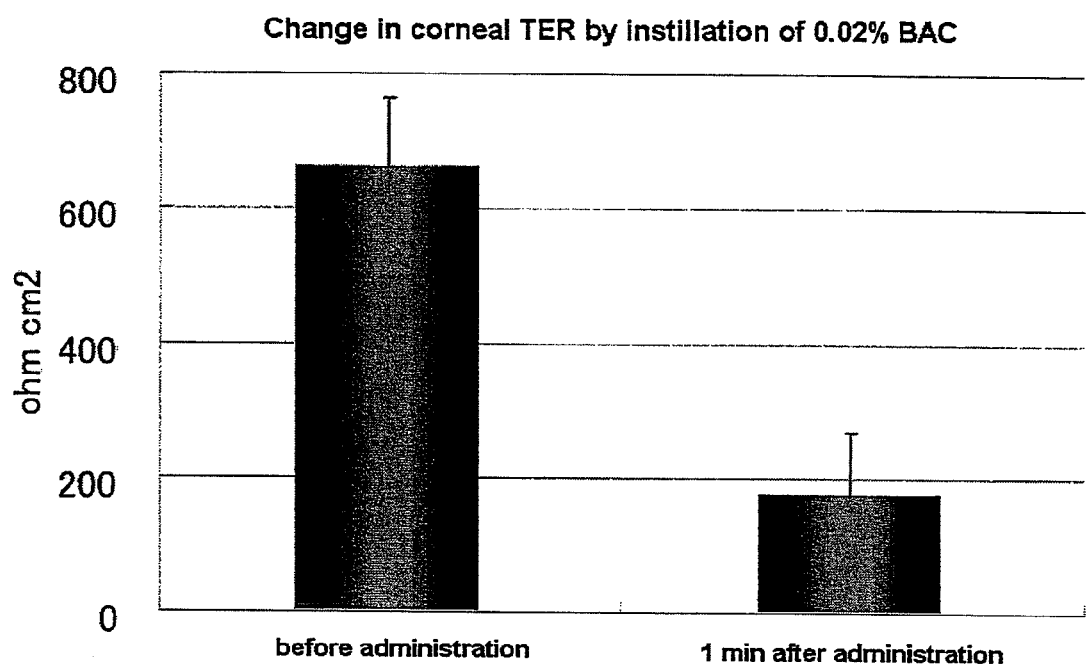
FIG. 8 shows measured TER values before the administration and 1 minute after the administration of 0.02% BAC, measured by the measuring device of FIG. 6 (n=3).

A 0.02% BAC was dropped onto the eye of the rabbit, and the resulting TER value was compared with the TER value before the administration. FIGS. 7 and 8 show the results. FIG. 7 shows that immediately after the TER measuring device has been contacted with the cornea, a TER can be measured. Prior to the BAC administration (indicated as "normal cornea" in FIG. 7) as well as after the BAC administration, within one second after the device was contacted with the cornea, a stable TER value could be measured. As shown in FIG. 8, one minute after the BAC administration, the TER was significantly reduced. This value was consistent with the results shown in FIG. 4.

When a corneal staining test was carried out to confirm the presence or absence of a corneal disorder before and after the TER measurement, hardly any corneal disorder was caused by the TER measurement using the present device (not shown).

While the invention has been described with emphasis on preferred embodiments thereof, it will be apparent to one skilled in the art that various changes and modifications can be made therein. The present invention can be practiced in a manner other than described specifically in the present specification. The present inventors intend that the present invention is understood to encompass all variations and modifications within the spirit and scope of the invention as defined by the appended CLAIMS.

INDUSTRIAL APPLICABILITY

The present invention provides a detection method for a corneal disorder that is less invasive to the living eye. Since the detection method according to the present invention requires no anterior chamber centesis, it is applicable even to human, and can be utilized for diagnosis and earlier treatment of a corneal disorder. Moreover, the method of the present invention makes it possible to carry out measurements within a short period of time after a corneal disorder and also to carry out over time measurements of a corneal disorder, and is useful for studies for drug screening, studies for evaluating efficacy of drugs, studies for evaluating influences of a drug to the eyes, and the like. Moreover, by using the method of the present invention, it becomes possible to obtain useful new findings with respect to corneal barrier functions in various corneal diseases, and consequently to contribute greatly to developments of the ophthalmology and ophthalmic medicine.

This application is based on a patent application No. 2008-052567 filed in Japan (filing date: Mar. 3, 2008), the contents of which are incorporated in full herein.

The invention claimed is:

1. A method for measuring a corneal transepithelial electric resistance value, comprising
   (1) placing electrodes on a cornea and a conjunctiva, wherein the electrodes are connected to a voltage-electric resistance value measuring device, and wherein the device flows an electric current through corneal epithelium, and
   (2) measuring the corneal transepithelial electric resistance value based on the electric current flowing through the corneal epithelium.

2. A method for measuring a corneal transepithelial electric resistance value comprising:
   (1) a step of preparing a voltage-electric resistance value measuring device, and a first electrode and a second electrode which are connected to the device;
   (2) a step of placing the first electrode on the cornea and the second electrode on the conjunctiva; and
   (3) a step of measuring the corneal transepithelial electric resistance value by flowing an electric current between the first electrode and the second electrode and through corneal epithelium to measure an electric resistance.

3. The method according to claim 1, wherein a periphery of the electrode placed on the cornea is insulated.

4. The method according to claim 1 which is carried out on a living eye.

5. A device for measuring a corneal transepithelial electric resistance on a living eye, which comprises:
(1) a first electrode suitable to be placed on a cornea,
(2) a second electrode suitable to be placed on a conjunctiva, ~d
(3) an insulator that insulates the first electrode, and
(4) a voltage-electric resistance value measuring device connected to the first electrode and the second electrode, wherein the device is capable of flowing an electric current through corneal epithelium, wherein the first electrode and the insulator are integrated, and wherein the insulator is made of silicone rubber, and the insulator has a contact surface to the cornea having the same curvature as that of the cornea.

6. The device according to claim 5, wherein the first electrode and the insulator are integrated via a conductor.

7. The device according to claim 5, wherein the second electrode is further integrated.

8. The device according to claim 5, wherein the second electrode is formed into a sheet shape.

9. The device according to claim 6, wherein the conductor is a gel of hyaluronic acid or atelocollagen.

10. The method according to claim 3 which is carried out on a living eye.

11. The method according to claim 2, wherein a periphery of the electrode placed on the cornea is insulated.

12. The method according to claim 2 which is carried out on a living eye.

* * * * *